US012716757B2

(12) United States Patent
Gindele et al.

(10) Patent No.: US 12,716,757 B2
(45) Date of Patent: Aug. 25, 2026

(54) TOOL-LESS REPLACEABLE GAS SENSOR MODULE

(71) Applicant: Rosemount Inc., Shakopee, MN (US)

(72) Inventors: Greg E. Gindele, Maple Lake, MN (US); Hun Chhuoy, Savage, MN (US); Ryan T. Lindsey, Eden Prairie, MN (US)

(73) Assignee: Rosemount Inc., Shakopee, MN (US)

( * ) Notice: Subject to any disclaimer, the term of this patent is extended or adjusted under 35 U.S.C. 154(b) by 228 days.

(21) Appl. No.: 15/392,388

(22) Filed: Dec. 28, 2016

(65) Prior Publication Data

US 2018/0058887 A1 Mar. 1, 2018

Related U.S. Application Data

(60) Provisional application No. 62/379,947, filed on Aug. 26, 2016.

(51) Int. Cl.
*G01D 11/24* (2006.01)
*G01N 33/00* (2006.01)

(52) U.S. Cl.
CPC ....... *G01D 11/245* (2013.01); *G01N 33/0009* (2013.01)

(58) Field of Classification Search
CPC ........... G01N 33/0009; G01N 33/0027; G01D 11/245; H01R 13/052; H01R 13/111; H01R 13/20; H01R 13/6273
See application file for complete search history.

(56) References Cited

U.S. PATENT DOCUMENTS 4,586,773 A * 5/1986 Lothmann .......... H01R 13/6272 439/348
5,055,270 A 10/1991 Consadori et al.
6,252,510 B1 6/2001 Dungan
6,629,858 B2 * 10/2003 Lo ...................... H01R 13/6471 439/108

(Continued)

FOREIGN PATENT DOCUMENTS

CN 103348057 A 10/2013
CN 104067455 A 9/2014

(Continued)

OTHER PUBLICATIONS

Detcon Hydrogen Sulfide Sensor Model DM-700-H2S Product Data Sheet, retrieved from http://www.detcon.com/1-documents/data_sheets/1-sensors/Model%20700/DM-700/Hydrogen%20Sulfide%20DM-700-H2S%20PDS.pdf, retrieved on Aug. 22, 2017, 2 pages.

(Continued)

*Primary Examiner* — Joshua T Kennedy
(74) *Attorney, Agent, or Firm* — Christopher R. Christenson; Kelly, Holt & Christenson, P.L.L.C.

(57) ABSTRACT

A gas sensor module includes a gas sensor configured to provide an electrical indication related to a gas. The gas sensor module also includes an alignment mechanism and a latching feature configured to couple the gas sensor module to a housing device. The gas sensor module also includes a pin guide configured to establish an electrical connection between a header of the housing device and the gas sensor. In addition, the gas sensor module is configured to be tool-lessly inserted into the housing device.

4 Claims, 5 Drawing Sheets

(56) References Cited

U.S. PATENT DOCUMENTS

| | | | | |
|---|---|---|---|---|
| 6,670,887 | B2 | 12/2003 | Dungan | |
| 6,794,991 | B2 | 9/2004 | Dungan | |
| 6,905,367 | B2 * | 6/2005 | Crane, Jr. | H01R 13/514 439/701 |
| 7,089,778 | B2 | 8/2006 | Rabenecker et al. | |
| 7,345,590 | B2 | 3/2008 | Nakano et al. | |
| 7,631,568 | B2 * | 12/2009 | Kilps | G01N 15/0227 73/863.33 |
| 8,358,105 | B2 | 1/2013 | Barten et al. | |
| 9,620,879 | B2 * | 4/2017 | Li | H01R 13/114 |
| 9,719,813 | B2 * | 8/2017 | Landis | G01D 11/245 |
| 2004/0134901 | A1 * | 7/2004 | Jeong | H05B 6/645 219/702 |
| 2004/0209507 | A1 * | 10/2004 | Starta | H01R 13/71 439/247 |
| 2005/0000271 | A1 | 1/2005 | Rabenecker et al. | |
| 2006/0266647 | A1 | 11/2006 | Khalafpour et al. | |
| 2009/0227132 | A1 * | 9/2009 | Bethurum | H01R 4/4821 439/153 |
| 2009/0230278 | A1 | 9/2009 | Tranquilli et al. | |
| 2010/0158758 | A1 | 6/2010 | Gustin | |
| 2010/0170794 | A1 * | 7/2010 | Gibson | G01N 27/4062 204/406 |
| 2011/0287655 | A1 * | 11/2011 | Lin | H01R 13/514 439/357 |
| 2012/0157018 | A1 * | 6/2012 | Robinson | G01D 11/24 455/127.1 |
| 2012/0282798 | A1 * | 11/2012 | Oe | B60L 11/1816 439/369 |
| 2015/0177206 | A1 | 6/2015 | Basham et al. | |
| 2015/0204830 | A1 | 7/2015 | Arunachalam | |
| 2015/0377658 | A1 * | 12/2015 | Landis | G01D 11/245 439/660 |
| 2024/0096528 | A1 * | 3/2024 | Malone | H01C 10/14 |

FOREIGN PATENT DOCUMENTS

| | | | |
|---|---|---|---|
| CN | 104769651 | A | 7/2015 |
| EP | 1437925 | A1 | 7/2004 |
| JP | 11339149 | A | * 12/1999 |
| JP | H11339149 | A | 12/1999 |
| JP | 2003043004 | A | 2/2003 |
| WO | WO 02/057764 | | 7/2002 |

OTHER PUBLICATIONS

Det-Tronics Electrochemical Toxic Gas Detector GT3000 Series Specification Data, retrieved from http://www.det-tronics.com/ProductCatalog/GasDetection/Documents/90-1199-10.1-GT3000.pdf, retrieved on Aug. 22, 2017, 2 pages.

International Search Report and Written Opinion for International Patent Application No. PCT/US2017/045038, dated Oct. 25, 2017, 15 pages.

Russian Office Action dated Oct. 30, 2019, for Russian Patent Application No. 2019108459, 16 Pages including English translation.

First Examination Report for Australian Patent Application No. 2017314914 dated Sep. 12, 2019, 3 pages.

First Office Action for Chinese Patent Application No. 201710107585.0 dated Sep. 29, 2019, 21 pages with English Translation.

Office Action dated Feb. 28, 2020 for Canadian Application No. 3035045, 5 pages.

Extended European Search Report dated Mar. 10, 2020 for European Application No. 17844100.2, 8 pages.

Second Examination Report, dated Apr. 8, 2020 for Australian Patent Application No. 2017314914. 3 pages.

Second Chinese Office Action dated Jul. 1, 2020 for Chinese application No. 201710107585.0, 32 pages with English translation.

Indian Examination Report for Indian patent application No. 201927007281 dated Sep. 21, 2020, 5 pages.

EPO Communication pursuant to Article 94(3) dated Nov. 19, 2020, for European Patent Application No. 17844100.2, 25 pages.

Second Office Action dated Dec. 10, 2020, for Canadian Patent Application No. 3035045. 4 pages.

Third Office Action for Chinese Patent Application No. 201710107585.0, dated Feb. 2, 2021, 29 pages including English translation.

Rejection Decision dated Jun. 2, 2021 for Chinese Patent Application No. 201710107585.0, 20 pages including English translation.

Third Office Action dated Sep. 22, 2021, for Canadian Patent Application No. 3035045, 5 pages.

Third Office Action for Mexican Patent Application No. MX/a/2019/002255, dated Jan. 3, 2023. 9 pages including English Translation.

Fourth Canadian Office Action dated Jul. 21, 2022. for Canadian Patent Application No. 3035045. 4 pages.

Mexican Office Action dated Jun. 21, 2022. for Mexican Patent Application No. MX/a/2019/002255, 1 page.

Second Office Action for Mexican Patent No. MX/a/2019/002255, Dated Aug. 30, 2022, 6 pages.

International Preliminary Report on Patentability for International Application No. PCT/US2017/045038, dated Oct. 25, 2017, 12 Pages.

Office Action for Canadian Patent Application No. 3035045, dated Jan. 18, 2024, 4 pages.

CA 3,035,045—Ofice Action, dated Dec. 10, 2024, 4 pages.

Office Action for Canadian Patent Application No. 3035045, Dated May 3, 2023, 4 pages.

* cited by examiner

TOOL-LESS REPLACEABLE GAS SENSOR MODULE

CROSS-REFERENCE TO RELATED APPLICATION

The present application is based on and claims the benefit of U.S. Provisional Patent Application Ser. No. 62/379,947, filed Aug. 26, 2016, which application is incorporated by reference in its entirety.

BACKGROUND

The process industry often employs gas sensors in order to detect the presence of a particular gas, often as part of a safety system. This is important as many gases may be harmful to human health and/or the environment. Industrial gas sensors are normally mounted near the process area of a plant or control room, or an area to be protected. Generally, industrial gas sensors are installed at fixed locations and a cable connects the gas sensors to a monitoring system.

SUMMARY

A gas sensor module includes a gas sensor configured to provide an electrical indication related to a gas. The gas sensor module also includes an alignment mechanism and a latching feature configured to couple the gas sensor module to a housing device. The gas sensor module also includes a pin guide configured to establish an electrical connection between a header of the housing device and the gas sensor. In addition, the gas sensor module is configured to be tool-lessly inserted into the housing device.

DETAILED DESCRIPTION OF ILLUSTRATIVE EMBODIMENTS

Gas sensors may be used to detect combustible, flammable and toxic gases. Gas sensors may include infrared point sensors, ultrasonic sensors, electrochemical gas sensors and semiconductor sensors. Over time, gas sensors often become depleted and need to be replaced. In order to replace a gas sensor, a known protocol is often followed requiring a number of different tools. Additionally, these protocols often require specific cables or an insertion point to be within a field of view of a user. This can prove quite cumbersome.

Contrary to conventional systems, embodiments described herein provide a tool-less, replaceable gas sensor module configured for insertion into a housing device, such that the electronics of the gas sensor module connect to the header of the transmitter without requiring any manual cable assembly. This allows a user to install and replace a depleted gas sensor without needing tools.

In addition, since at least some process installations may involve highly volatile, or even explosive, environments, it is often beneficial, or even required, for devices that operate in such environments to comply with intrinsic safety requirements. These requirements help ensure that compliant electrical devices will not generate a source of ignition even under fault conditions. One example of an Intrinsic Safety requirement is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998.

Figure 1:
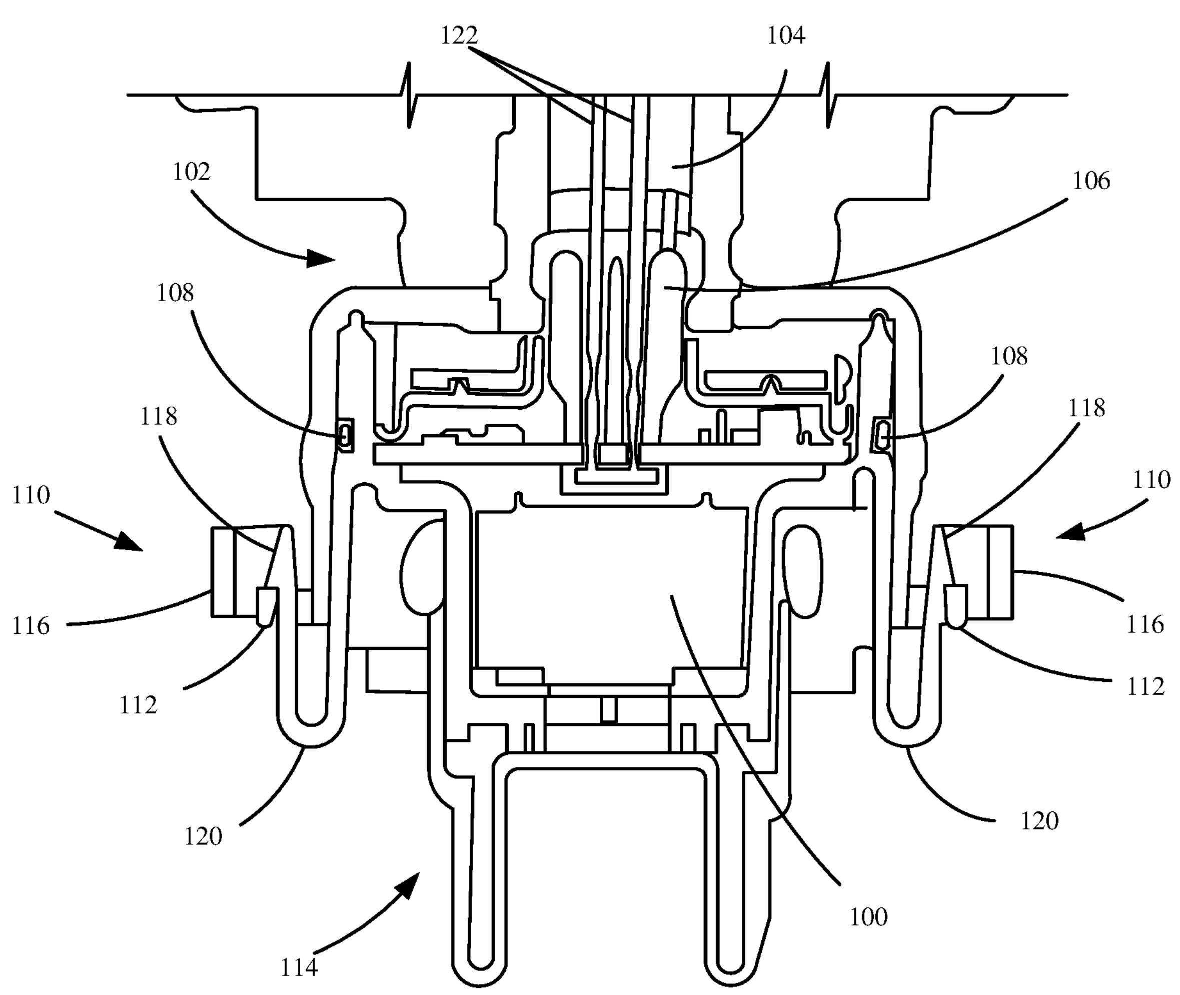
FIG. 1 shows a cross sectional view of a gas sensor module within a housing device in accordance with an embodiment of the present invention.

FIG. 1 shows a cross sectional view of a gas sensor module within a housing device in accordance with an embodiment of the present invention. Gas sensor module 114 includes gas sensor 100 and, in one embodiment, includes latching features 110 configured to latch to a latching point 112 of a housing device 102. In one embodiment, a mechanical latching, between latching features 110 and latching point 112, allows gas sensor module 114 to be securely fastened within housing device 102. Gas sensor module 114 may also include, in one embodiment, a pin guide 106 configured to electrically couple gas sensor 100 to header 104 of housing device 102. Header 104 may comprise any number of connecting pins 122. In one embodiment, the connection between pin guide 106 and header 104 establishes an electrical connection between gas sensor 100 of gas sensor module 114 and housing device 102 without any manual cable assembly or even needing to see an insertion point during installation. Gas sensor module 114 may also include a sealing mechanism 108. In one embodiment, sealing mechanism 108 is configured to create a seal between gas sensor module 114 and housing device 102. Sealing mechanism 108 can be, for example, an O-ring.

Latching features 110 allow for a secure fastening of gas sensor module 114 to housing device 102. Latching features 110, in one embodiment, may have a hooked shape flexible body 120 extending outwardly from gas sensor module 114 with an inclined end portion 118. In one embodiment, a tab 116 may be attached to inclined end portion 118 and hooked shape body 120 and provide a mechanism for compressing latching features 110. In operation, latching features 110 may be inserted into latching point 112 through an applied insertion force until inclined end portion 118 rests on top of latching point 112, at which point gas sensor module 114 is fastened within housing device 102.

In one embodiment, latching features 110 may also facilitate the release of gas sensor module 114 from housing device 102. A compression force may be applied to latching feature 110 to decouple latching feature 110 from latching point 112. Gas sensor module 114 may then be removed from housing device 102 such as when gas sensor module 114 is replaced.

Pin guide 106, in one embodiment, establishes an electrical connection between gas sensor module 114 and housing device 102. Pin guide 106 may be positioned at a top of gas sensor module 114 and may comprise any number of apertures configured to receive connecting pins 122 of housing device 102. In one embodiment, pin guide 106 may automatically receive connecting pins 122 upon the insertion of gas sensor module 114 into housing device 102. In one embodiment, two pins are used as shown in FIG. 1. However, it is expressly contemplated that pin guide 106 may comprise any number of connecting pins 122 configured to be received in header 104.

Sealing mechanism 108 may be positioned within gas sensor module 114 such that a seal is created when gas sensor module 114 is inserted into housing device 102. In one embodiment, sealing mechanism 108 is an O-ring. However, it is expressly contemplated that other sealing mechanisms may be used in accordance with other embodiments.

Figure 2:
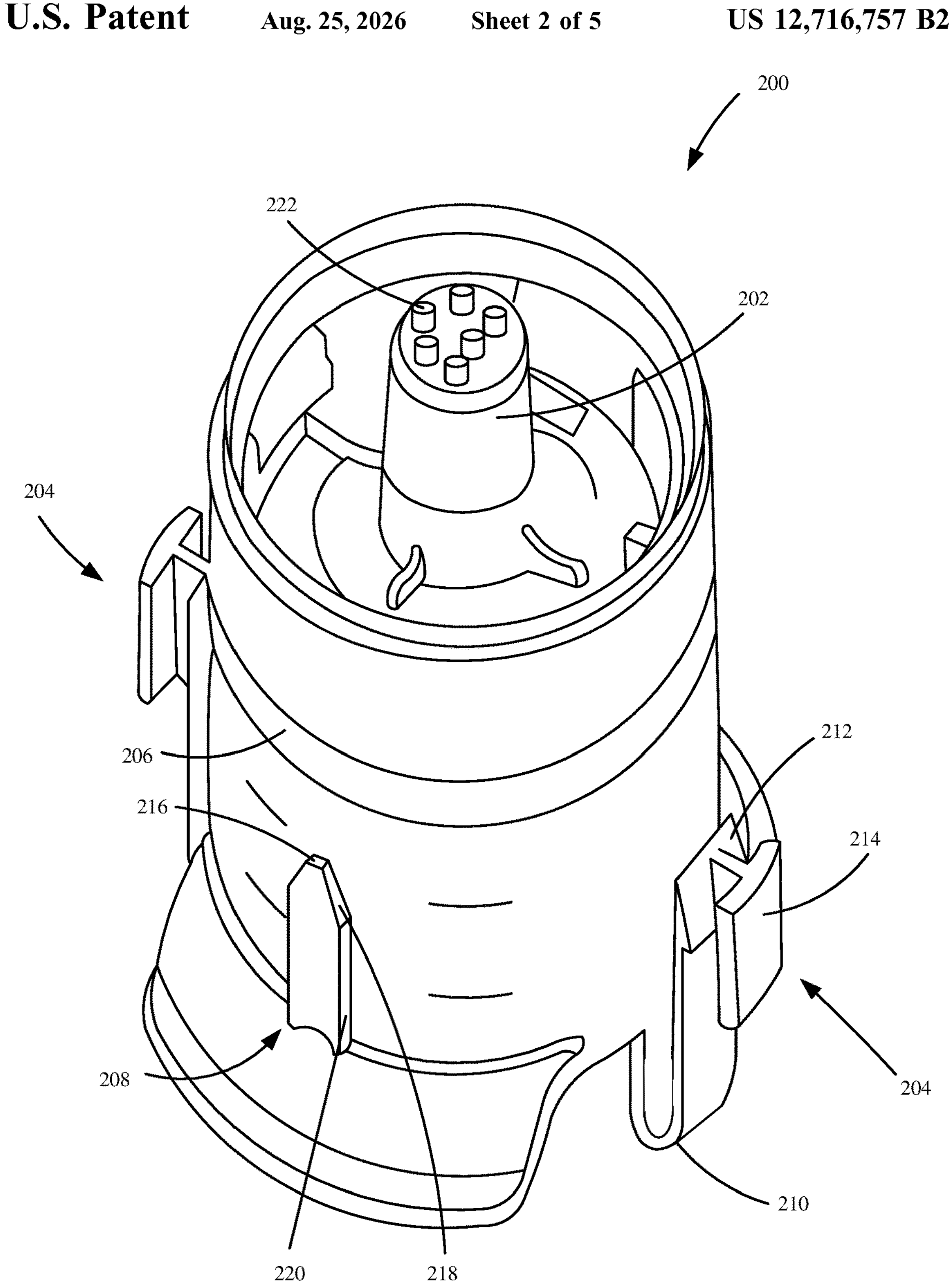
FIG. 2 is a diagrammatic view of a gas sensor module in accordance with an embodiment of the present invention.

FIG. 2 is a diagrammatic view of a gas sensor module in accordance with an embodiment of the present invention. Gas sensor module 200 includes pin guide 202, latching features 204, and alignment mechanism 208 configured to allow gas sensor module 200 to be inserted into a housing device (e.g. housing device 102 shown in FIG. 1) without requiring any tools. Pin guide 202, in one embodiment, is configured to connect to a header (e.g. header 104 shown in FIG. 1) of a housing device upon insertion of gas sensor module 200 into the housing device.

In one embodiment, latching features 204 comprise a hooked shape flexible body 210, an inclined portion 212 and a tab 214. Latching features 204 may latch to a latching point (e.g. latching point 112 of FIG. 1) of a housing device.

Alignment mechanism 208, in one embodiment, is configured to align with a corresponding aligning portion on a housing device.

Gas sensor module 200 may also include a sealing mechanism 206. In one embodiment, sealing mechanism 206 is an O-ring. Sealing mechanism 206 may be located within or about a body of gas sensor module 200 and, when inserted into a housing device, create a seal between gas sensor module 200 and the housing device.

Prior to the insertion of gas sensor module 200 into a housing device (e.g. housing device 102 in FIG. 1), alignment mechanism 208 may, in one embodiment, orient pin guide 202 such that pin guide 202 may couple to a header (e.g. header 104 in FIG. 1) of a housing device. Specifically, upon aligning alignment mechanism 208 with a corresponding alignment portion on a housing device, apertures 222 of pin guide 202 may be in a correct orientation to connecting pins (e.g. connecting pins 122 in FIG. 1). An insertion force may then be applied to gas sensor module 200 such that pin guide 202 receives connecting pins of a housing device thereby establishing an electrical connection with connecting pins of a housing device.

In one embodiment, alignment mechanism 208 comprises a protrusion extending radially from an outside diameter of gas sensor module 200. Alignment mechanism 208 may include a protrusion with a flattened top portion 216, a tapered portion 218 and a linear side portion 220. Flattened top portion 216, tapered portion 218 and linear side portion 220 are configured to align gas sensor module 200, when inserted into a housing device (e.g. housing device 102 in FIG. 1). For example, flattened top portion 216, tapered portion 218 and linear side portion 220 may rotate along with gas sensor module 200 until aligned with a corresponding alignment portion such as a groove or channel on a housing device. An insertion force may be applied to gas sensor module 200, allowing alignment mechanism 208 to be axially received by a corresponding alignment portion on a housing device. In one embodiment, corresponding alignment portion may be a slot configured to receive alignment mechanism 208.

In other embodiments, alignment mechanism 208 may be unique to a particular type of gas sensor module 200. For example, but not by limitation, this may include a hydrocarbon gas sensor module having a different alignment mechanism than a non-hydrocarbon based gas sensor module. This might ensure that a particular gas sensor module is installed into an appropriate, corresponding housing device and not installed in a non-corresponding housing.

Figure 3A:
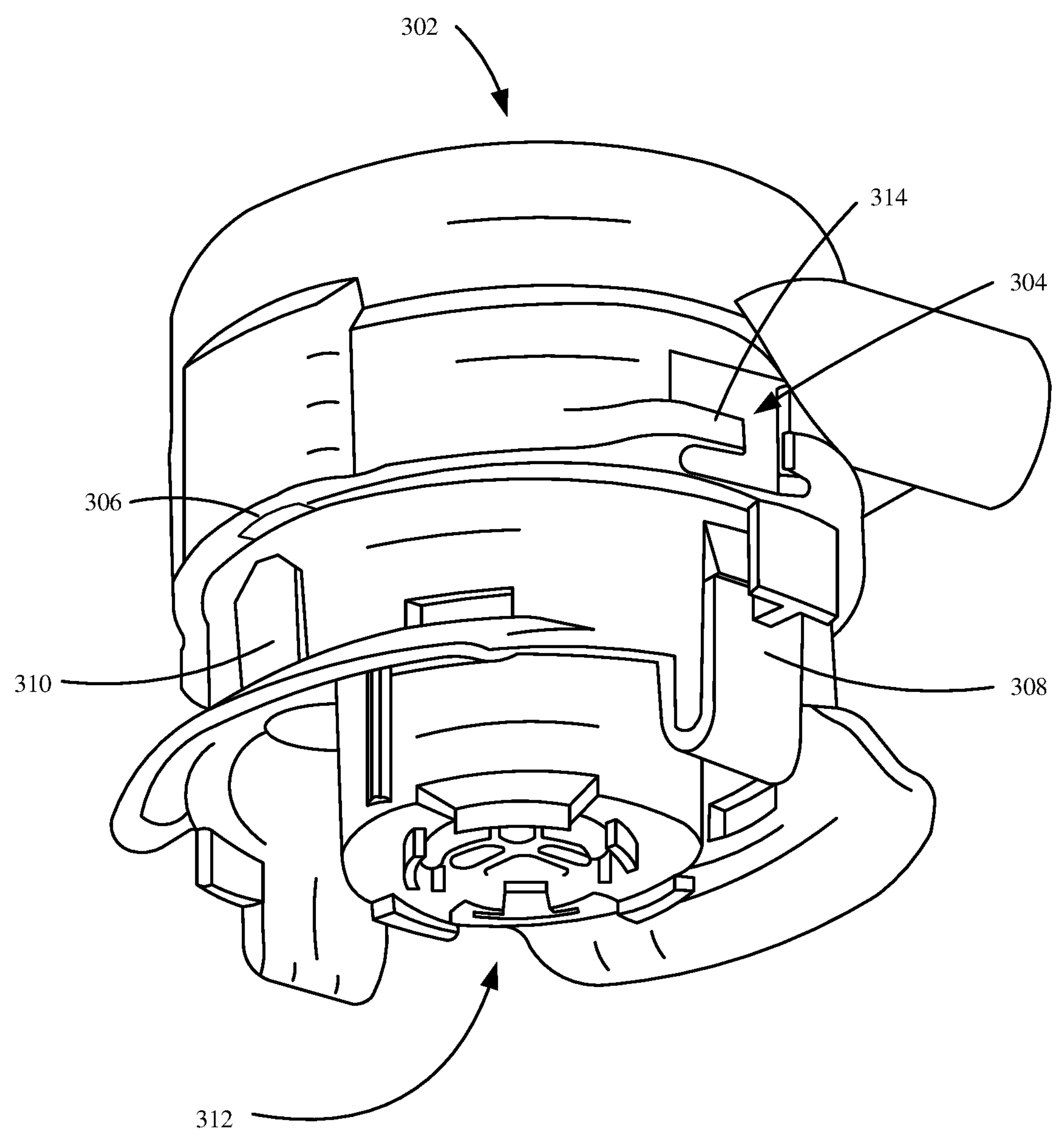
FIGS. 3A and B are diagrammatic views of a gas sensor module aligned with a housing device in accordance with an embodiment of the present invention.
Figure 3B:
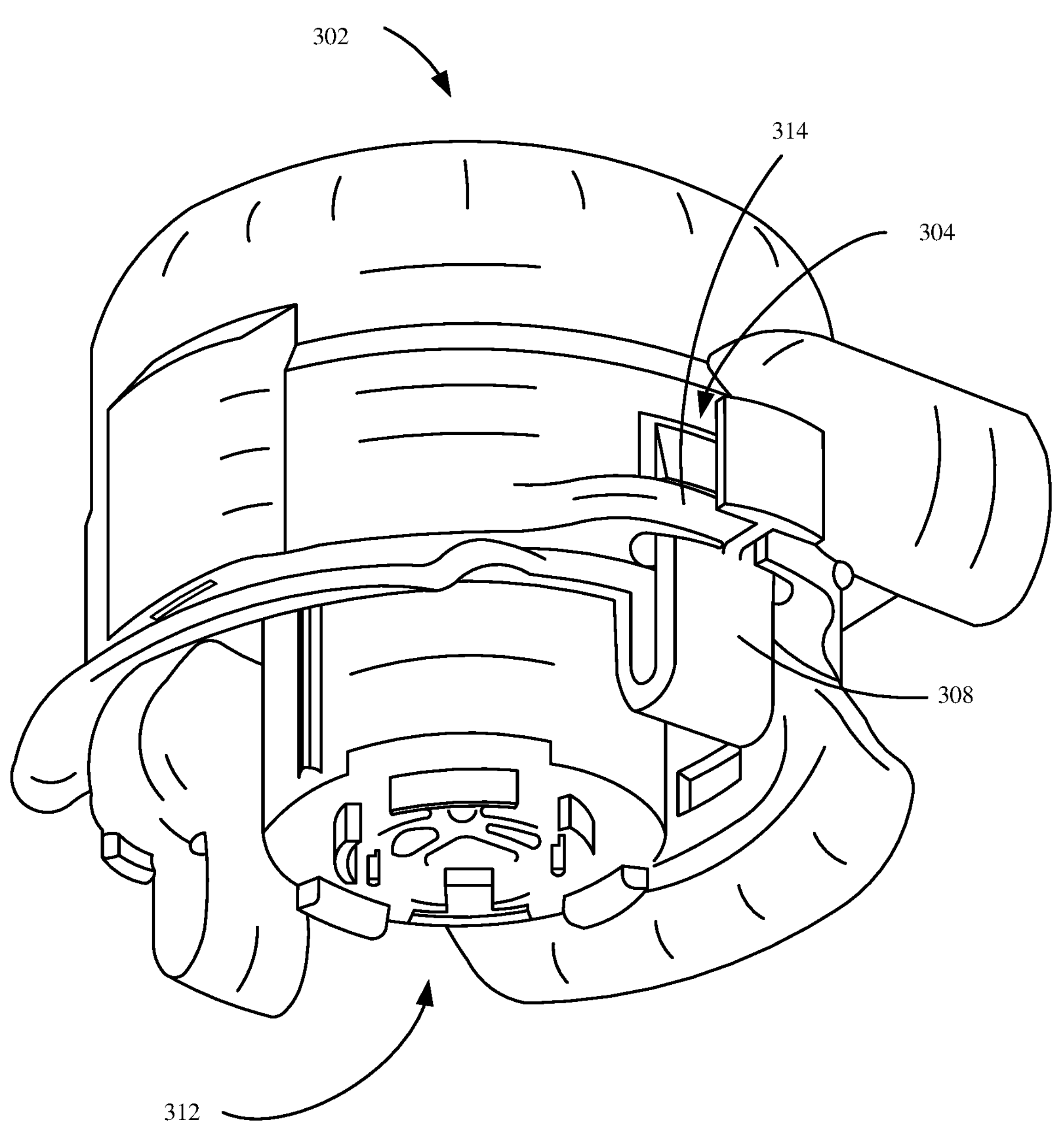

FIGS. 3A and 3B are diagrammatic views of a gas sensor module aligned with a housing device in accordance with an embodiment of the present invention. FIG. 3A illustrates a gas sensor module aligned with a housing device. Gas sensor module 312 includes an alignment mechanism 310. In one embodiment, alignment mechanism 310 is a protrusion that extends outwardly from a body of gas sensor module 312, and is configured to align with and be received by a corresponding alignment portion 306 of a housing device 302. Gas sensor module 312, in one embodiment, includes a latching feature 308 configured to latch to latching point 304 of housing device 302. In one embodiment, latching point 304 may include at least one extended section 314 configured to engage latching feature 308.

FIG. 3B illustrates a gas sensor module assembly. As shown, gas sensor module 312 includes latching feature 308 coupled to latching point 304 of housing device 302. Latching point 304 includes extended sections 314 that engage latching feature 308. Once latching feature 308 is coupled to latching point 304, gas sensor module 312 is fastened to housing device 302.

Figure 4:
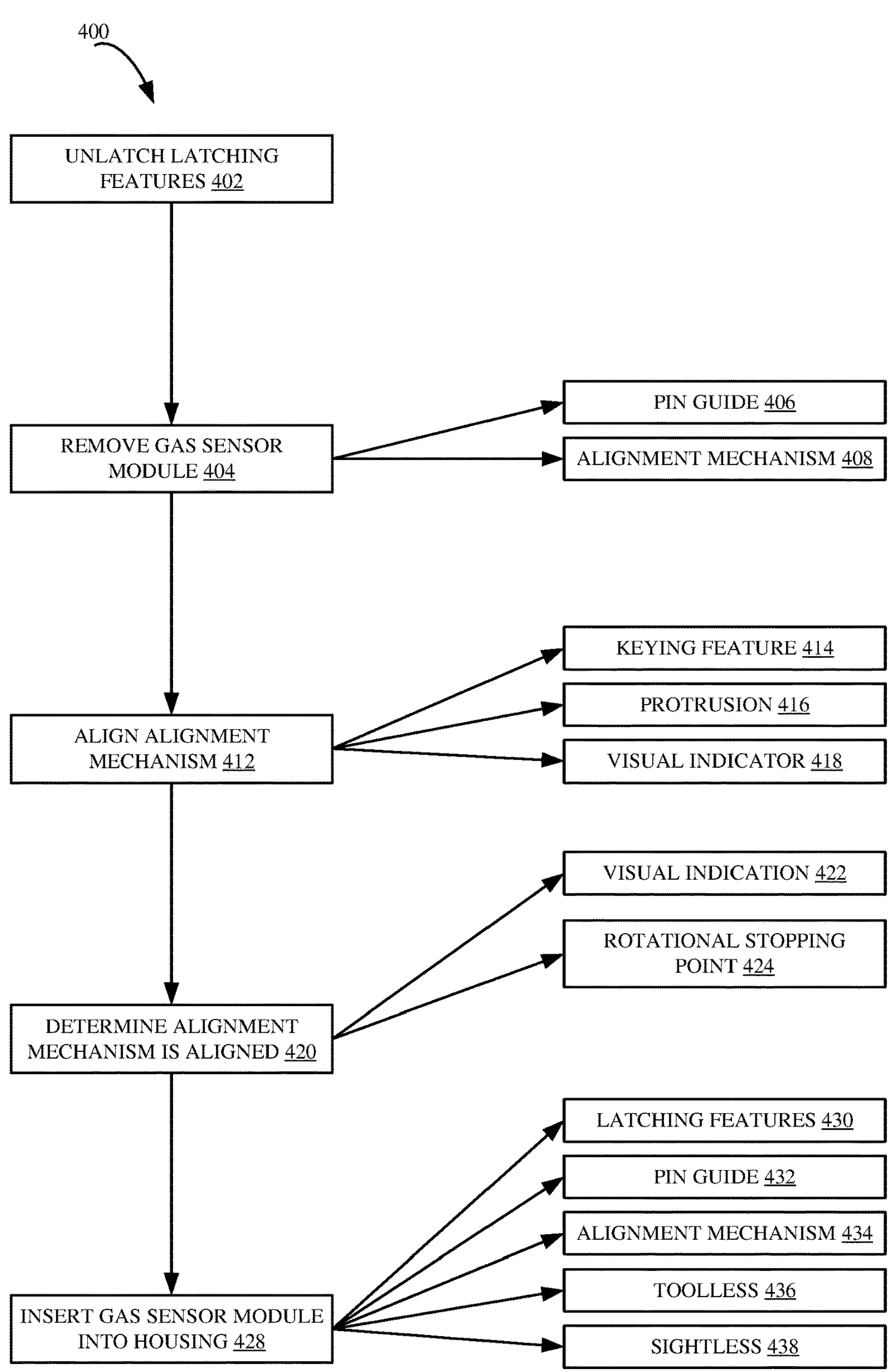
FIG. 4 is a flow diagram of a method of replacing a depleted gas sensor module in accordance with an embodiment of the present invention.

FIG. 4 is a flow diagram of a method of replacing a depleted gas sensor module in accordance with an embodiment of the present invention. Method 400 may be useful for replacing a depleted gas sensor module without needing tools, having to manually connect cables, or having an insertion point be within a field of view of a user. Method 400 begins at block 402 where a user unlatches a latching feature of an installed gas sensor module. In one embodiment, unlatching allows latching features to temporarily deform. Next, at block 404, the user removes the gas sensor module from its housing. In one embodiment, upon applying a pulling force, gas sensor module becomes completely disconnected from housing device. The pulling force may disengage a pin guide, as indicated in block 406, of the gas sensor module from a header of housing device. The pulling force may also disengage an alignment mechanism, as indicated in block 408, of gas sensor module from a corresponding alignment portion of housing device.

At block 412, a user aligns an alignment mechanism of a new gas sensor module with a corresponding alignment portion of the housing device. The alignment mechanism may comprise a keying feature, as indicated in block 414, configured to be received by corresponding alignment portion of housing device. In one embodiment, the keying feature includes a unique shape that may only insert into a corresponding alignment portion. In one embodiment, the alignment mechanism comprises a protrusion, as indicated in block 416, on gas sensor module body. The protrusion may comprise a substantially uniform shape configured to be received by corresponding alignment portion. In one embodiment, the alignment mechanism may comprise a visual indicator, as indicated in block 418, that may include a color or a pattern on gas sensor module.

At block 420, a user determines that an alignment mechanism of a new gas sensor module is aligned with a corresponding alignment portion of a housing device. The determination may include a visual indication, as indicated in block 422. The visual indication may include an actuated light or a pattern that forms when alignment mechanism is aligned with corresponding alignment portion of housing device, for example. In another embodiment, a determination may include a rotational stopping point, as indicated in block 424. As gas sensor module is rotated relative to housing device, the rotational stopping point may cease rotational movement of the gas sensor module once alignment mechanism and corresponding alignment portion are aligned. In addition, other detection mechanisms are envisioned in other embodiments.

At block 428, a user inserts a gas sensor module into a housing device. In one embodiment, an insertion force is applied to axially displace the gas sensor module relative to the housing device until latching features of gas sensor module latch to a latching point of housing device, as indicated in block 430. In one embodiment, the gas sensor module is securely fastened within housing device upon a mechanical latching of latching features to a latching point. As gas sensor module is inserted into housing device, a pin guide of gas sensor module connects to a header of housing device, as indicated in block 432. Additionally, as gas sensor module is inserted into housing device, an alignment mechanism of gas sensor module is received by a corresponding alignment portion of housing device, as indicated in block 434. The insertion of gas sensor module into housing device is done without requiring any tools, as indicated in block 436. In one embodiment, the insertion of gas sensor module into housing device is done without an insertion point needing to be within a field of view of a user, as indicated in block 438.

Method 400 allows a user to replace a depleted gas sensor module without having to follow a particular protocol requiring significant amounts of time or a variety of tools. Additionally, method 400 allows a user to replace a depleted gas sensor module without having to manually connect cables or have an insertion point be within a field of view of a user.

Although the present invention has been described with reference to preferred embodiments, workers skilled in the art will recognize that changes may be made in form and detail without departing from the spirit and scope of the invention.

What is claimed is:

1. A gas sensor system comprising:

a housing device comprising:

a pair of latching points;

a housing alignment portion;

a header; and a gas sensor module sealingly coupled to the housing device, the gas sensor module comprising:

a body having a pair of latching features configured to couple the body to the pair of latching points of the housing device, wherein a first latching feature of the pair of latching features is disposed diametrically opposite from a second latching feature of the pair of latching features, each latching feature having a barb portion that engages a respective latching point, a tab support extending away from the barb portion, and a tab mounted to the tab support, such that upon application of a compression force upon each tab, each barb will disengage from each respective latching point, wherein each latching point of the housing device includes a slot configured to pass the tab support, and wherein each latching feature includes a hook-shaped flexible body;

a gas sensor mounted within the body and configured to provide an electrical indication related to a gas;

a gas sensor alignment feature extending radially from an outer diameter of the body and being configured to engage the housing alignment portion;

a pin guide configured to connect to the header;

wherein the gas sensor alignment feature and the pin guide are spaced apart;

wherein the gas sensor alignment feature includes protrusion having a flattened top portion, a tapered portion and a linear side portion, wherein the flattened top portion, the tapered portion and the linear side portion are configured to align the gas sensor module, when inserted into the housing device, so that the flattened top portion, the tapered portion and the linear side portion rotate along with the gas sensor module until aligned with the corresponding alignment portion of the housing device.

2. The gas sensor module assembly of claim 1, and further comprising an indicator of a type of the gas sensor module.

3. The gas sensor module assembly of claim 1, wherein each latching point further comprises an extended section configured to interact with a respective latching feature.

4. The gas sensor module assembly of claim 1, wherein the header further comprises connecting pins configured to be received in the pin guide of the gas sensor module.

* * * * *